United States Patent [19]

Sterzel et al.

[11] Patent Number: 5,453,365
[45] Date of Patent: Sep. 26, 1995

[54] PREPARATION OF LACTATES

[75] Inventors: Hans-Josef Sterzel, Dannstadt-Schauernheim; Herbert Vogel, Ludwigshafen; Herbert Exner, Waldsee; Detlef Kratz, Heidelberg; Martin Brudermüller, Mannheim, all of Germany

[73] Assignee: BASF Aktiengesellschaft, Ludwigshafen, Germany

[21] Appl. No.: 342,002

[22] Filed: Nov. 16, 1994

[30] Foreign Application Priority Data

Dec. 8, 1993 [DE] Germany .......................... 43 41 770.1

[51] Int. Cl.⁶ .................................. C12P 7/62; C12P 7/56
[52] U.S. Cl. ............................................ 435/135; 435/139
[58] Field of Search ........................................ 435/135, 139

[56] References Cited

U.S. PATENT DOCUMENTS

| 4,444,881 | 4/1984 | Urbas | 435/139 |
| 4,771,001 | 9/1988 | Bailey et al. | 435/139 |
| 5,210,296 | 5/1993 | Cockrens et al. | 562/589 |
| 5,252,473 | 10/1993 | Walkup et al. | 435/139 |
| 5,071,954 | 12/1991 | Walkup et al. | 435/139 |

FOREIGN PATENT DOCUMENTS

WO91/11527 8/1991 WIPO .
WO93/0040 1/1993 WIPO .

*Primary Examiner*—Herbert J. Lilling
*Attorney, Agent, or Firm*—Keil & Weinkauf

[57] ABSTRACT

A process for the preparation of lactates by fermentation of mixtures containing sugars, conversion of the lactic acid obtained during fermentation to its salts, followed by esterification, in which a) there is added to the fermentation liquor an alkaline earth metal carbonate or bicarbonate so as to neutralize the resultant lactic acid to a degree of at least 90 mol %, b) the resulting fermentation liquor is adjusted to pH 7 to 13 by the addition of $NH_3$ and $CO_2$ and the resultant precipitates are separated, and c) the resulting, purified ammonium lactate solution is esterified with an alcohol.

8 Claims, 1 Drawing Sheet

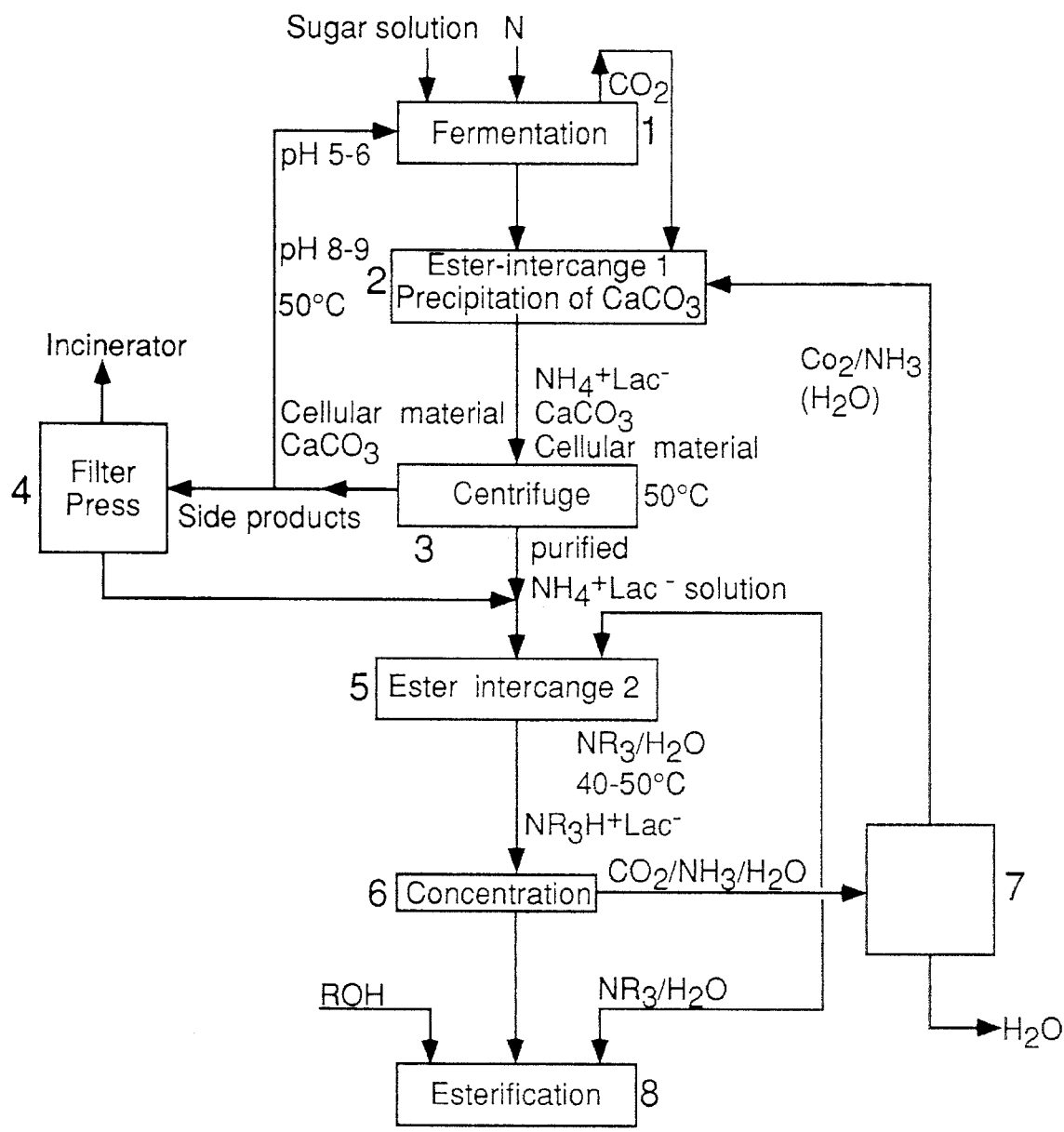

PREPARATION OF LACTATES

The invention relates to a process for the preparation of lactates by fermentation of mixtures containing sugars, conversion of the lactic acid obtained during fermentation to its salts, followed by esterification.

Lactates are important intermediates for the preparation of lactide (I)

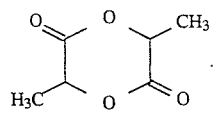

Lactide, particularly l- or d-lactide, has great industrial significance as monomeric material for the preparation of polylactides by ring-opening polymerization of the monomers.

Polylactides are thermoplastic and have high-grade mechanical properties and good barrier properties against the intrusion of steam and oxygen. Under usual composting conditions they are quickly hydrolyzed to lactic acid and are further degraded by bacterial action to form water and carbon dioxide. For this reason polylactides show a growing potential as degradable packaging material.

Optically pure lactides are prepared from fermentation lactic acid. The synthesis processes known in the art have some serious drawbacks, however.

According to the state of the art, dilute solutions of fermentable sugar are fermented by lactic acid bacteria to produce l- or d-lactic acid, depending on bacterium species. Since free lactic acid in concentrations greater than 1 wt % inhibits fermentation, the lactic acid must be neutralized, for which purpose primarily calcium and/or magnesium carbonate are usually employed. When the concentration is sufficiently high the Ca and/or Mg lactates can, following separation of the cellular substance, be crystallized out by cooling the fermentation liquor and thus be partially separated from the fermentation liquor. The free lactic acid is obtained by causing the lactates to react with concentrated sulfuric acid. This means however that approximately the same quantity of sulfates is produced as that of lactic acid, which sulfates must be disposed of, so that the waste balance of the compostable polylactides is unfavorably influenced.

One process has been described which does not exhibit this drawback (WO 91/11527). In this process the fermentation liquor is neutralized with ammonia. Then the cellular substance of the fermentation liquor is separated. To the ammonium lactate solution there is added an alcohol and the mixture is exposed to from 150 to 170 bar of carbon dioxide at temperatures ranging from 160° C. to 180° C.

During this treatment ammonium bicarbonate is formed as is also the appropriate lactate, which is removed by distillation. But this process has other serious drawbacks: when effecting neutralization of the fermentation liquor with ammonia maximum lactic acid concentrations in the fermentation liquor of only 8–10 wt % are achieved. This means that the ammonia process is must be relegated from the outset to a low space-time yield process. In addition, expensive high-pressure equipment is required. The constituents of the mixture of water, lactates and alcohol must be separated from each other without the occurrence of hydrolysis, in order to avoid any reverse reaction taking place via hydrolysis of the lactates.

In another published patent application (WO 93/00440) the preparation of lactates or lactic acid from a fermentation liquor is described. In said reference the lactic acid formed is neutralized with ammonia and, following separation of the biomass, the ammonium lactate solution is concentrated by evaporation of the water. To the concentrated ammonium lactate solution there is added sulfuric acid so as to liberate lactic acid and cause partial crystallization of ammonium sulfate. The lactic acid is esterified with a $C_4$–$C_5$ alcohol with separtion of water and the ester is then purified and processed further.

Thus this process also suffers from the drawback of having to accept lower space-time yields in the fermentation when effecting neutralization of the lactic acid with ammonia. Moreover, a large amount of ammonium sulfate is produced as waste material.

It was thus the object of the invention to provide a process for the preparation of lactates which does not exhibit the aforementioned drawbacks and which, in particular, can be carried out at high space-time yields with little need for elaboration on apparatus and process engineering measures.

This object is achieved with the process defined above, wherein a) there is added to the fermentation liquor an alkaline earth metal carbonate or bicarbonate so as to neutralize the resultant lactic acid to a degree of at least 90 mol %, b) the resulting fermentation liquor is adjusted to pH 7 to 13 by the addition of $NH_3$ and $CO_2$ and the resultant precipitates are separated, and c) the resulting, purified ammonium lactate solution is esterified with an alcohol.

A preferred embodiment of the process comprises adding to the ammonium lactate solution, prior to the esterification of process step c), a tertiary alkylamine in order to form a trialkylammonium lactate solution, which is then in turn esterified with the alcohol.

In this embodiment the amount of tertiary amine added to the ammonium lactate is preferably at least equimolar thereto.

Another preferred embodiment of this process comprises concentrating the alkylammonium lactate solution prior to the esterification, in which case it has been found to be advantageous to recycle the $NH_3$ and $CO_2$ given off during concentration to the process step b). It is particularly advantageous to carry out the process continuously. A special advantage of the process of the invention process resides in the fact that the process steps a) and b) can be carried out substantially without changing the temperature of the reaction mixture. Finally, the tertiary amine liberated during esterification can be recycled to the process. The reaction of the calcium lactate with the CO2 and $NH_3$ taking place in process step b) can be illustrated as follows:

$$Ca(Lac)_2 + CO_2 + 2NH_3 + H_2O \rightarrow 2NH_4Lac + CaCO_3$$

BRIEF DESCRIPTION OF DRAWING

The FIGURE represents a flow sheet for a preferred embodiment of the process of the invention.

The first step consists in the fermentation of a solution of molasses, whey, sugar or a mixture thereof having sugar contents of from 5 to 15 % in the fermenter (1). To this end, use is made, in known manner (cf e.g. WO 91/11527), of bacteria of the genus lactobacillus, which produce lactic acid either in the d form or in the l form to a high degree of optical purity.

To the fermentation batch there can be admixed, as nutrients for the bacteria, a complex nitrogen source, vitamins and salts (preferably phosphates). The fermentation reactor (1) ideally has the residence time characteristics of a flow tube. Fermentation takes place in particular at temperatures ranging from 37° to 60° C.

In process step a) the resultant lactic acid is pH controlled by pumping in an aqueous mash of calcium carbonate and/or magnesium carbonate or a mash of the bicarbonates so as to neutralize the acid to an extent of at least 90 mol %, preferably 95 mol %. During fermentation, the pH is kept constant at preferably 4 to 6, in particular at 5.5. Following an adequate residence time of from 2 to 20 h the fermentation liquor is withdrawn from the fermenter and is passed, without applying or removing heat, to the first ester interchange stage (2), i.e. to the process step b).

There the carbon dioxide evolved in the fermenters is passed through the fermentation liquor and concurrently the ammonia coming from a subsequent process step is added. The stream of ammonia is regulated in such a manner that a pH of from 7 to 13, in particular of from 8.0 to 9.5 is maintained in (2). By this means calcium or magnesium carbonate is precipitated in the presence of the cellular substance and of disturbing accompanying substances and the alkaline earth metal lactate is converted to ammonium lactate. This means that the high space-time yield achieved by neutralization with a divalent base remains and the equivalent amount of ammonium lactate is obtained without losses.

In this case the otherwise disturbing metabolism products are adsorbed on the crystallizing calcium or magnesium carbonate and for the most part precipitated therewith. Moreover, the calcium or magnesium carbonate surprisingly considerably improves the separation of the solids mixture, e.g. in a filter or centrifuge (3). Process step b) can be effected in a cascade of stirred boilers or flow tubes.

Preferably, the quantity of carbon dioxide added, e.g., by fumigation in a closed circuit at pressures of from 1 to 3 bar, is such that the content of free $Ca^{2+}$ or $Mg^{2+}$ does not exceed $5\text{-}10^4$ mol/L; so that all of the lactate is caused to react. Any excess ammonium (hydrogen) carbonate present is decomposed in the concentrating stage to produce carbon dioxide and ammonia, which are recycled to the first ester interchange stage (2).

The reaction mixture remains at low viscosity in all stages. In addition, the single-stage separation of the solid materials (3) takes place without temperature change and thus without additional consumption of thermal energy. A small part of the mash of cellular substance, Ca or Mg carbonate and metabolism products of from 1 to 20% is removed from the circuit via filtration equipment (4) and then dehydrated. This material can be used as silage starter in agricultural applications, or it is destroyed by burning.

The mother liquor obtained during dehydration contains ammonium lactate and is added to the filtrate.

The ammonium lactate solution thus obtained can be passed to the second ester interchange stage, step (5), where it is mixed with a tertiary alkylamine. The molar ratio of tertiary amine to $NH_4^+$ is preferably from 1:1 to 1.2:1. The admixture takes place without additional cooling or heating, for example, in a stirred boiler or flow tube, i.e. it is thermally neutral. Preferred tertiary amines of the formula $NR_1R_2R_3$ ($R=C_1\text{-}C_6$alkyl) are such as have boiling points above that of water, for example, tripropylamine or tributylamine. In the following step (6) the solution from stage (2) can be concentrated by the application of thermal energy, preferably in a number of steps, with the removal, by distillation, of water, ammonia and excess carbon dioxide. Water is separated from carbon dioxide and ammonia in column (7), and the carbon dioxide and ammonia, which can still contain small amounts of water, are passed to step (2). Care should be taken to ensure that no organic tertiary amine passes into step (2), as it could interfere with the fermentation via the recycled moist cellular substance.

The purified ammonium lactate solution or the, optionally concentrated, solution containing $NR_3H^+Lac^-$ as desirable substance is passed to the esterification stage (8), i.e. to the process step c), where it is esterified with a monohydric alcohol, in particular an alcohol containing 2 to 10 C atoms, e.g. 1-butanol, 1-pentanol, or 1-hexanol, or an alcohol of higher molecular weight. e.g. a long-chain monohydric or dihydric alcohol containing more than 10 C atoms, branched diols or polyols such as longer-chain homologs of pentaerythritol or in particular poly(ethylene oxide)s having molecular weights of from 180 to 1000 g/mol, such as $HO\text{---}(CH_2\text{---}CH_2\text{---}O)_n\text{---}CH_2CH_2\text{---}CH_2\text{---}OH$ in which n is equal to 2–25, preferably in the absence of a catalyst at so temperatures of from 70° C. to 200° C. under standard pressure or in vacuo (from 1 to 1000 mbar, preferably from 15 to 200 mbar). When the $NR_3H^+Lac^-$ solution is used, the tertiary amine, in admixture with water, is removed by distillation and recycled to step (5). The esterification is carried out preferably in a cascade of stirred boilers having a common vapor hood. To effect esterification, a molar ratio of alcohol to lactic acid of from, say, 0.5:1 to 5:1 can be used.

The exchange of $NH_4^+$ for $NR_2H^+$ can be carried out, in particular, in order to avoid, during esterification, the formation of lactic acid amide in a side-reaction and thus to avoid corresponding losses of yield. The mixture of lactates and excess alcohol can be separated by distillation.

The lactates of the invention can, optionally following transesterification, be caused to react with e.g. a higher alcohol to form lactide. The formation of lactide, known per se, comprises an internal transesterification, in which the first alcohol used for the esterification is again liberated and can be recycled to the process.

The process of the invention is favorable and advantageous from a process engineering aspect, for various reasons:

There is no need for energy to be consumed for cooling the fermentation liquor to effect crystallization of the calcium lactate, and no capital outlay is necessary for a crystallizer and refrigeration plant.

Using a pure sugar solution there is obtained, downstream of the evaporator (6), a concentrated ammonium lactate solution containing less than 1 wt % of by-products, based on the dissolved ammonium lactate.

Fermentation takes place at high space-time yields with the consequent advantages of low capital expenditure and energy costs: during neutralization in step a) lactic acid concentrations of from 13 to 15 wt % are achieved. Raw materials, nutrients and metabolism products can for the most part be recycled to the process, which in turn increases the yield: no high-pressure equipment is required, no high viscosity streams occur: only a small number of pieces of equipment is required.

Due to the mild reaction conditions high optical purities can be achieved.

EXAMPLES

The examples described below were carried out batchwise as far as the fermentation stage.

Fermentation (process step a)

80 g of dry brewer's yeast are sterilized with 5 L of water in a fermenter having a capacity of 15 L. To this there is added, following cooling to 50° C., a previously separately sterilized solution of 120 g of glucose, 10 mL of concentrated phosphoric acid and 0.3 g of Tween 80 (ICI) in 5 L of drinking water. The culture is inoculated with 100 mL of a not more than 12 hours' old culture of *lactobacillus casei*, ATCC 27,139, grown in MRS medium (3rd Appl. Bacteriol. 23, 13 (196)).

The fermentation liquor is stirred at 50° C. at a rate of 250 rpm with the addition of $CaCO_3$. After approximately 20 to 24 h the culture is switched over from batch to continuous mode of operation.

At this point the Ca lactate concentration is 85 to 110 g/L. The switch-over to continuous operation takes place by adding fresh medium having the composition described above. The inflow of fresh medium and of lye ($CaCO_3$ suspension) necessary to maintain a constant pH is adjusted such that the residence time is 15.5 h. The product concentration in the effluent of ferment is ca 12 wt % based on lactic acid.

First Ester Interchange Stage (process step b)

18.9kg of a fermentation liquor as described above and having a content of calcium lactate which is equivalent to ca 12 wt % of lactic acid (equivalent to ca 25.2 mol of lactic acid) are kept at 50° C. at a starting pH of 5.2.

Over a period of 40 min there are added to the liquor with vigorous stirring 430 g of ammonia and ca 570 g of carbon dioxide. At the commencement of the reaction the pH rises to 9.4 but drops to 8.2 during the reaction. Further introduction of $CO_2$ causes no further decrease in pH. During the reaction the brown liquor lightens to a beige color on account of the formation of calcium carbonate. The reaction mixture retains its low viscosity. After the stirrer has been stopped the solid material settles much faster than the cellular substance of the pure fermentation liquor.

The mixture of solids can be isolated by filtration from the reaction mixture, again at ca 50° C., quickly and unproblematically. Following washing with a little water there are obtained 2.76 kg of moist filter cake. The weight of the dried filter cake is 1.40 kg and the amount of calcium carbonate therein is 1.25 kg.

The ammonium lactate solution thus obtained can be passed directly to the esterification stage, but it can, if desired, be first subjected to another ester interchange.

Second Ester Interchange Stage (optional)

1000 g of a 15% strength solution of ammonium lactate are mixed with triethylamine in stoichiometric amounts (200 mL=1.5 mol) and the mixture is refluxed for 3 h. The escaping ammonia is absorbed in water in a wash bottle.

The triethylammonium lactate solution thus obtained has a content of 26.3 wt % of $Et_3NH$—Lac. The solution can be immediately used for esterifications.

Esterification Stage (process step c)

a) 500 g of $NH_4$ lactate solution are concentrated in vacuo (100 mbar, 43° C.). Ca 270 g of water are evaporated off.

The remaining solution contains ca 0.5 mol of $NH_4$ lactate. This is esterified with 120 g of pentanol (ca 1.5 mol) and esterification is continued with removal of water until no more water can be detected.

The esterification mixture remaining at the bottom of the column is subsequently fractionally distilled at 100 mbar. This leads to a yield of, in all, 72.3 g of distilled pentyl lactate, which is equivalent to a yield of 90.4%.

b) 357 g of an 80% strength solution of l-ammonium lactate (2.7 mol) and 200 g of triethylene glycol (1.33 mol) are combined. A water/ammonia mixture is removed by distillation with stirring at 160° C. in a Vigreux column. A vacuum of 20 mbar is then applied at the same temperature and distillation is continued. There are obtained, in all, 95 g of $H_2O$ (conversion=80%). The product contains the following chief components (% by area (GC)) and can be used for the preparation of lactide:

Lactic acid 1%, lactide 6%, triethylene glycol 12%, triethylene glycol monolactate 39%, triethylene glycol dilactate 28%.

c) Example b) is repeated using the following materials: 179 g (1.35 mol) of 80% strength ammonium lactate, 276 g (0.67 mol) of Lutrol E400 [poly(ethylene glycol) $C_{18}H_{38}O_{10}$].

There are obtained 51 of distillate (conversion=85% ).

The mixture, as examined by GC analysis, contains lactic acid (2.4%), lactide (35%), Lutrol E400 (29%) and Lutrol mono- and di-lactates. The crude mixture can be used for the preparation of lactide.

d) Ca 300 mL of triethylammonium lactate (TEAL) (95% strength solution), obtained by a second ester interchange (as described above), are placed in a stirred vessel. The solution is heated slowly. At ca 115° C. thermal dissociation of the lactate is complete. Triethylamine and water can be removed by azeotropic distillation. The internal temperature is raised further to ca 180° C. and n-pentanol (240 mL/h) and TEAL (88 g/h, 95%) are then metered in continuously. Excess alcohol and pentyl lactate are withdrawn continuously as overheads. The distillate contains in addition to triethylamine, water, n-pentanol, and 25% of n-pentyl lactate (equivalent to a yield of 95%).

e) 747 g of an 80%strength solution of l-triethylammonium lactate (3.5 mol) and 186 g of diethylene glycol (1.75 mol) are combined. A mixture of water and triethylamine (360 g) is distilled off with stirring at 120° C. in vacuo (40 mbar) in a Vigreux column.

The temperature is then raised to 140° C. after which a further 112 g of $NEt_3/H_2O$ are distilled off (conversion= 95%).

The product contains the following chief components (% by area (GC)) and can to be used for the preparation of lactide:

Diethylene glycol 2%, lactide 19%, diethylene glycol monolactate 22%, diethylene glycol dilactate 57%.

We claim:

1. A process for the preparation of lactates by fermentation of mixtures containing sugars, conversion of the lactic acid obtained during fermentation to its salts, followed by esterification, wherein a) there is added to the fermentation liquor an alkaline earth metal carbonate or bicarbonate so as to neutralize the resultant lactic acid to a degree of at least 90 mol %, b) the resulting fermentation liquor is adjusted to pH 7 to 13 by the addition of $NH_3$ and $CO_2$ and the resultant precipitates are separated, and c) the resulting, purified ammonium lactate solution is esterified with an alcohol.

2. A process as defined in claim 1, wherein, prior to the esterification of process step c), the ammonium lactate solution is esterified with a tertiary alkylamine to form an alkylammonium lactate solution.

3. A process as defined in claim 2, wherein the alkylammonium lactate solution is concentrated prior to the esterification.

4. A process as defined in claim 3, wherein the $NH_3$ and $CO_2$ separated during concentration are recycled to the process step b).

5. A process as defined in claim 1, which is carried out continuously.

6. A process as defined in claim 2, wherein the ammonium lactate is esterified in process step c) with at least an equimolar amount of a tertiary amine.

7. A process as defined in claim 1, wherein the process steps a) and b) are carried out without substantial modification of the temperatures of the reaction mixture.

8. A process as defined in claim 2, wherein the tertiary amine liberated during esterification in process step c) is recycled to the process.

* * * * *